(12) United States Patent
Hashimoto et al.

(10) Patent No.: US 7,192,964 B2
(45) Date of Patent: Mar. 20, 2007

(54) 4-OXOIMIDAZOLIDINE-2-SPIROPIPERIDINE DERIVATIVES

(75) Inventors: Masaya Hashimoto, Tsukuba (JP); Osamu Okamoto, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/484,765

(22) PCT Filed: Jul. 18, 2002

(86) PCT No.: PCT/JP02/07292

§ 371 (c)(1),
(2), (4) Date: Jan. 23, 2004

(87) PCT Pub. No.: WO03/010168

PCT Pub. Date: Feb. 6, 2003

(65) Prior Publication Data

US 2005/0004363 A1     Jan. 6, 2005

(30) Foreign Application Priority Data

Jul. 23, 2001     (JP) ............................. 2001-220919

(51) Int. Cl.
*A61K 31/438*     (2006.01)
*C07D 471/10*     (2006.01)

(52) U.S. Cl. ........................ 514/278; 546/20
(58) Field of Classification Search ................ 546/20; 514/278
See application file for complete search history.

(56) References Cited

U.S. PATENT DOCUMENTS 6,043,366 A    3/2000    Adam et al.

FOREIGN PATENT DOCUMENTS

| EP | 997464 | 10/1999 |
| JP | 1-207291 | 8/1989 |
| JP | 2000-169476 | 6/2000 |
| WO | 00/34280 | 6/2000 |
| WO | 01/96337 | 12/2001 |

OTHER PUBLICATIONS

Francois Jenck et al., "Orphanin FQ acts as an anxiolytic to attenuate behavioral responses to stress", Proceedings of the National Academy of Sciences of the United States, 94, pp. 14854-14858, 1997.
Anna Rizzi et al., "Characterization of the locomotor activity-inhibiting effect of nociceptin/orphanin FQ in mice" Naunyn-Schmiedeberg's Archives of Pharmacology, 363, pp. 161-165, 2001.
Francois Jenck et al., "A synthetic agonist at the orphanin FQ/nociceptin receptor ORL1: Anxiolytic profile in the rat", Proceedings of the National Academy of Sciences of the United States of America, 97, pp. 4938-4943, 2000.
Charles N. Allen et al., "Orphanin-FQ/Nociceptin (OFQ/N) Modulates the Activity of Suprachiasmatic Nucleus Neurons", Journal of Neuroscience, 19, pp. 2152-2160, 1999.
Graeme Henderson et al., "The orphan opioid receptor and its endogenous ligand-nociceptin/orphanin FQ", TiPS, 18, pp. 293-300, 1997.
David Julius, "Home for an orphan endorphin", Nature, 377, p. 476, 1995.
Axel Fischer et al., "Nociceptin-Induced Inhibition of Tachykinergic Neurotransmission in Guinea Pig Bronchus", Journal of Pharmacology & Experimental Therapeutics, 285, pp. 902-907, 1998.
Hunter C. Champion et al., "Nociceptin, a novel endogenous ligand for the $ORL_1$ receptor, has potent erectile activity in the cat", American Journal of Physiology, 273, pp. E214-E219, 1997.
Zbigniew K. Krowicki et al., "Orphanin FQ/nociceptin and [$Phe^1$ $\phi(CH_2$ -NH)$Gly^2$ ]nociceptin(1-13)-$NH_2$ stimulate gastric motor function in anaesthetized rats", British Journal of Pharmacology, 130, pp. 1639-1645, 2000.

*Primary Examiner*—Rita Desai
(74) *Attorney, Agent, or Firm*—Wenderoth, Lind & Ponack, L.L.P.

(57) ABSTRACT

The invention relates to 4-oxoimidazolidine-2-spiropiperidine derivatives represented by a general formula [I]

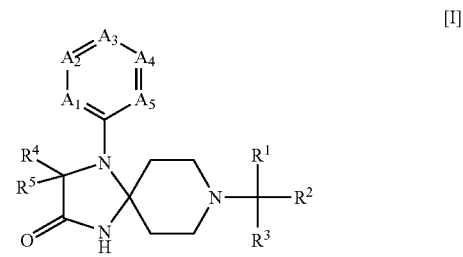

[in which $A_1$, $A_2$, $A_3$, $A_4$ and $A_5$ stand for optionally halogen-substituted methine, or nitrogen atom; $R^1$ and $R^2$ stand for lower alkyl or the like; $R^3$ stands for hydrogen or lower alkyl; $R^4$ and $R^5$ stand for hydrogen, or lower alkyl which is optionally substituted with hydroxy, or the like] or salts thereof. These compounds act as nociceptin receptor agonist, and are useful as analgesic, reliever from tolerance to narcotic analgesic, reliever from dependence on narcotic analgesic, analgesic enhancer, antiobestic, drug for ameliorating brain function, remedy for schizophrenia, drug for treating regressive neurodegenerative diseases, antianxiety agent or antidepressant and remedy for diabetes insipidus and polyuria; and the like.

10 Claims, No Drawings

4-OXOIMIDAZOLIDINE-2-SPIROPIPERIDINE DERIVATIVES

TECHNICAL FIELD

This invention relates to 4-oxoimidazolidine-2-spiropiperidine derivatives which are useful in the field of medicines. Said compounds act as agonist for nociceptin receptor ORL1, and are useful as analgesic, reliever from tolerance to narcotic analgesic represented by morphine; reliever from dependence on narcotic analgesic represented by morphine; analgesic enhancer; antiobestic; drug for ameliorating brain function; remedy for schizophrenia; drug for treating regressive neurodegenerative diseases represented by Parkinsonism and chorea; antianxiety agent or antidepressant; remedy for diabetes insipidus; remedy for polyuria; remedy for hypotension; anesthetic or anesthetic adminiculum; remedy for sleep disorders represented by insomnia including increased sleep latency, intermittent wakefulness and decreased sleep efficiency; remedy for circadian rhythm disorder such as jet lag; drug for improving erectile function; airway dilation during dyspenea such as asthma or antitussive; or as drug for ameliorating motility of digestive tract during hypokinesis of digestive tract.

BACKGROUND ART

Nociceptin (the same substance as orphanin FQ) is a peptide composed of 17 amino acids and having a similar structure to that of opioid peptide. Nociceptin has an augmenting activity on reaction against noxious stimulae, an appetite stimulating activity, an activity for reducing a space learning ability, an antagonism against an analgesic action of classic opiate agonists, a dopamine release inhibitory action, a water diuresis action, a vasodilative action, a systemic blood pressure-lowering action and cell excitation inhibitory action, and it is considered to take part in controlling pain, appetite and memory, learning or emotional function through nociceptin receptor in the brain [refer to *Nature*, 1995, 377, 532; *Society for Neuroscience*, 1996, 22, 455; *NeuroReport*, 1997, 8, 423; *Eur. J. Neuroscience*, 1997, 9, 194; *Neuroscience*, 75, 1 and 333; and *Life Sciences*, 1997, 60, PL15 and PL141].

Further, it is known that morphine tolerance is reduced in knockout mice in which expression of nociceptin receptor is inhibited (*Neuroscience Letters*, 1997, 237, 136).

Heretofore known pharmacological activities of nociceptin or nociceptin receptor agonist from various reports include the following.

1) Administration of nociceptin was shown to have reduced reactivity to anxiety and stress (*Proceedings of the National Academy of Sciences of the United States of America*, 1997, 94, 14854–14858), which suggested nociceptin's having antianxiety or antidepressing action.

2) Nociceptin and nociceptin receptor agonist were shown to produce reduction of motor activity and sedation (*Naunyn-Schmiedeberg's Archives of Pharmacology*, 2001, 363, 161–165; *Proceedings of the National Academy of Sciences of the United States of America*, 2000, 97, 4938–4943). Nociceptin is also known to affect photosynchronization of biological clock (*Journal of Neuroscience*, 1999, 19, 2152–2160), which suggest its controlling role over sleep-and-waking cycle and circadian rhythm.

3) Nociceptin receptor agonist is known to show analgesia at spinal level (*Tips*, 1997, 18, 293–300). It was furthermore suggested to show little addictive tendency as highly active analgesic (*Nature*, 1995, 377, 476).

4) Nociceptin is known to inhibit airway contraction caused by substance P which induces airway contraction during inflammation such as asthuma or chronic airway obstruction (*Journal of Pharmacology & Experimental Therapeutics*, 1998, 285, 902–907), which suggests its effect to improve dyspenea induced by inflammatory airway contraction or antitussive effect.

5) Nociceptin is shown to increase cavernosal pressure at corpus cavernosum penis tissue to cause erection (*American Journal of Physiology*, 1997, 273, E214–E219), which suggests improvement of erectile dysfunction.

6) Nociceptin has accelerating action on motility of digestive tract (*British Journal of Pharmacology*, 2000, 130, 1639–1645), suggesting its ameliorating motility of digestive tract dysfunction such as hypokinesis of digestive tract.

Accordingly, compounds having nociceptin receptor agonist activities are presumed to act as analgesic, reliever from tolerance to narcotic analgesic represented by morphine; reliever from dependence on narcotic analgesic represented by morphine; analgesic enhancer; antiobestic; drug for ameliorating brain function; remedy for schizophrenia; drug for treating regressive neurodegenerative diseases represented by Parkinsonism and chorea; antianxiety agent or antidepressant; remedy for diabetes insipidus; remedy for polyuria; remedy for hypotension; anesthetic or anesthetic adminiculum; remedy for sleep disorders represented by insomnia including increased sleep latency, intermittent wakefulness and decreased sleep efficiency; remedy for circadian rhythm disorder such as jet lag; drug for improving erectile function; airway dilation during dyspenea such as asthma or antitussive; or as drug for ameliorating motility of digestive tract during hypokinesis of digestive tract.

On the other hand, nociceptin receptor agonists are disclosed, for example, in JP 2000-128879A or EP 963987A2, but they all are structurally different from 4-oxoimidazolidine-2-spiropiperidine derivatives of the present invention.

Also as compounds analogous of 4-oxoimidazolidine-2-spiropiperidine derivatives of the present invention, for example, WO 00/34280 pamphlet discloses nociceptin receptor inhibitor. However, the compounds shown in WO 00/34280 contain a —CH(R)—Cy (wherein Cy stands for an aliphatic carbocyclic group and R stands for hydrogen or lower alkyl) binding to nitrogen atom in a heterocyclic ring including piperidine ring, from which compounds of the present invention differ in the point that branched alkyl is bound to the nitrogen atom in piperidine ring. Furthermore, WO 00/34280 does not suggest selection of specific branched chain alkyl as the substituent to bind to the nitrogen atom in 4-oxoimidazolidine-2-spiropiperidine derivatives imparts nociceptin receptor agonist action to the compounds.

That is, compounds characterized in that piperidine is spiro-bound at 2-position of 4-oxoimidazoline ring and either a branched chain alkyl is bound to the nitrogen atom in the piperidine ring or an aliphatic carbocyclic group is directly bound to the nitrogen atom, are heretofore unknown. Nor it is known that 4-oxoimidazolidine-2-spiropiperidine derivatives having such a branched chain act specifically as nociceptin receptor agonist.

The objects of this invention are to provide the compounds having nociceptin receptor agonist action and also to provide analgesic, reliever from tolerance to narcotic analgesic represented by morphine; reliever from dependence on narcotic analgesic represented by morphine; analgesic enhancer; antiobestic; drug for ameliorating brain function; remedy for schizophrenia; drug for treating regressive neurodegenerative diseases represented by Parkinsonism and chorea; antianxiety agent or antidepressant; remedy for diabetes insipidus; remedy for polyuria; remedy for hypotension; anesthetic or anesthetic adminiculum; remedy for sleep disorders represented by insomnia including increased sleep latency, intermittent wakefulness and decreased sleep efficiency; remedy for circadian rhythm disorder such as jet lag; drug for improving erectile function; airway dilation during dyspenea such as asthma or antitussive; or as drug for ameliorating motility of digestive tract during hypokinesis of digestive tract, which act based on the pharmacological activity as nociceptin receptor agonist.

DISCLOSURE OF THE INVENTION

We have made concentrative studies on compounds having agonist activity on nociceptin receptors, to discover that 4-oxoimidazolidine-2-spiropiperidine derivatives having specific branched alkyl on the nitrogen atom in the piperidine ring are novel substances heretofore disclosed in no prior art literature and they specifically act as nociceptin receptor agonist. The present invention is completed based on these discoveries.

Namely, the present invention relates to:
(1) 4-oxoimidazolidine-2-spiropiperidine derivatives or salts thereof, which are represented by a general formula [I]

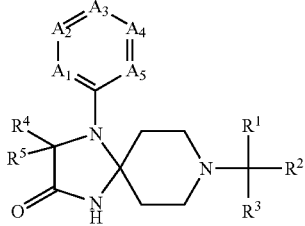

[in which $A_1, A_2, A_3, A_4$ and $A_5$ each independently stands for optionally halogen-substituted methine or nitrogen;
$R^1$ and $R^2$ each independently stands for lower alkyl, or $R^1$ and $R^2$ are combined to form $C_3$–$C_{12}$ aliphatic carbocyclic ring group together with the carbon atom to which they bind;
$R^3$ stands for hydrogen or lower alkyl;
$R^4$ and $R^5$ each independently stands for hydrogen or optionally hydroxyl- or amino-substituted lower alkyl].
(2) The compounds or salts thereof as described in (1), in which $A_1, A_2, A_3, A_4$ and $A_5$ each independently stands for optionally halogen-substituted methine.
(3) The compounds or salts thereof as described in (1), in which $A_1, A_2, A_3, A_4$ and $A_5$ are unsubstituted methine groups.
(4) The compounds or salts thereof as described in (1), in which $R^1$ is methyl, and $R^2$ is n-butyl or 2,2-dimethylpropyl.
(4') The compounds or salts thereof as described in any one of (1)–(3), in which $R^1$ is methyl and $R^2$ is n-butyl or 2,2-dimethylpropyl.
(5) The compounds or salts thereof as described in (1), in which $R^1$ is ethyl and $R^2$ is n-butyl or 2,2-dimethylpropyl.
(5') The compounds or salts thereof as described in any one of (1)–(3), in which $R^1$ is ethyl and $R^2$ is n-butyl or 2,2-dimethylpropyl.
(6) The compounds or salts thereof as described in (4) or (5), in which $R^3$ is hydrogen or methyl.
(6') The compounds or salts thereof as described in (4') or (5'), in which $R^3$ is hydrogen or methyl.
(7) The compounds or salts thereof as described in (1), in which $R^1$ and $R^2$ are combined to form decahydronaphthalene together with the carbon atom to which they bind, and $R^3$ is hydrogen.
(7') The compounds or salts thereof as described in any one of (1)–(3), in which $R^1$ and $R^2$ are combined to form decahydronaphthalene together with the carbon atom to which they bind, and $R^3$ is hydrogen.
(8) The compounds or salts thereof as described in (1), in which both $R^4$ and $R^5$ are hydrogen.
(8') The compounds or salts thereof as described in any one of (1)–(7), in which both $R^4$ and $R^5$ are hydrogen.
(9) The compounds or salts thereof as described in (1), in which either one of $R^4$ and $R^5$ is hydrogen and the other is hydroxyl-substituted lower alkyl.
(9') The compounds or salts thereof as described in any one of (1)–(7), in which either one of $R^4$ and $R^5$ is hydrogen and the other is hydroxyl-substituted lower alkyl.
(10) The compounds or salts thereof as described in (9), in which the lower alkyl of $R^4$ or $R^5$ is methyl or ethyl.
(10') The compounds or salts thereof as described in (9'), in which the lower alkyl of $R^4$ or $R^5$ is methyl or ethyl.
(11) The compounds or salts thereof as described in (1), in which the 4-oxoimidazolidine-2-spiropiperidine derivatives are 4-(3-fluorophenyl)-3-(2-hydroxyethyl)-8-(1,1,3,3-tetramethylbutyl)-1,4,8-triazaspiro[4.5]decan-2-one, 4-(3-fluorophenyl)-8-(1,1,3,3-tetramethylbutyl)-1,4,8-triazaspiro[4.5]decan-2-one, 4-phenyl-8-(1,1,3,3-tetramethylbutyl)-1,4,8-triazaspiro[4.5]decan-2-one, 4-phenyl-8-(1-ethylpentyl)-1,4,8-triazaspiro[4.5]decan-2-one, or 8-decahydronaphthalen-2-yl-4-phenyl-1,4,8-triazaspiro[4.5]decan-2-one.
(12) Pharmaceutical compositions containing the compounds or salts thereof as described in (1).
(13) Nociceptin receptor agonists containing the compounds or salts thereof as described in (1) as the active ingredient.
(14) Analgesic, reliever from tolerance to narcotic analgesic; reliever from dependence on narcotic analgesic; analgesic enhancer; antiobestic; drug for ameliorating brain function; remedy for schizophrenia; drug for treating regressive neurodegenerative diseases; antianxiety agent or antidepressant; remedy for diabetes insipidus; remedy for polyuria; remedy for hypotension; anesthetic or anesthetic adminiculum; remedy for sleep disorders or circadian rhythm disorder; drug for improving erectile function; airway dilator or antitussive; or as drug for ameliorating motility of digestive tract, which contain the compounds or salts thereof as described in (1) as the active ingredient.
(15) A method of producing 4-oxoimidazolidine-2-spiropiperidine derivatives or salts thereof represented by the general formula [I]

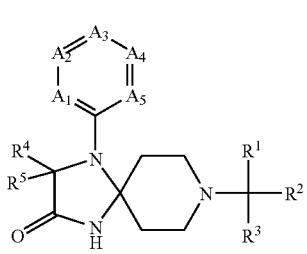

[I]

[in which $R^1$, $R^2$, $R^3$, $R^4$, $R^5$, $A_1$, $A_2$, $A_3$, $A_4$ and $A_5$ have the earlier given significations], which comprises 1) a step of subjecting a compound of a general formula [II]

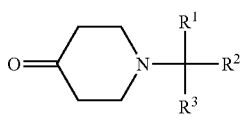

[II]

[in which $R^1$, $R^2$ and $R^3$ have the earlier given significations] and a compound of a general formula [III]

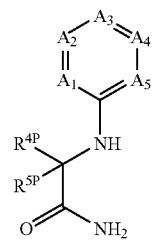

[III]

[in which $R^{4P}$ and $R^{5P}$ stand for hydrogen or lower alkyl optionally having optionally protected hydroxyl or optionally protected amino group; and $A_1$, $A_2$, $A_3$, $A_4$ and $A_5$ have the earlier given significations]

to dehydrative condensation, preferably in the presence of an acid; and 2) a step of removing the protective group(s), where the compound as obtained in 1) above contains protective group(s).

(16) A method of producing 4-oxoimidazolidine-2-spiropiperidine derivatives or salts thereof represented by a general formula [Ia]

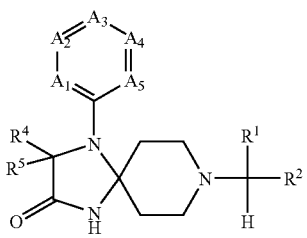

[Ia]

[in which $R^1$, $R^2$, $R^4$, $R^5$, $A_1$, $A_2$, $A_3$, $A_4$ and $A_5$ have the earlier given significations], which comprises 1) a step of subjecting a compound of a general formula [V]

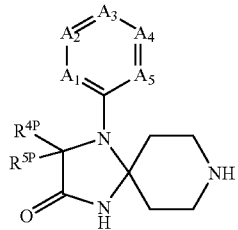

[V]

[in which $R^{4P}$, $R^{5P}$, $A_1$, $A_2$, $A_3$, $A_4$ and $A_5$ have the earlier given significations]

and a compound of a general formula [IV]

[IV]

[in which $R^1$ and $R^2$ have the earlier given significations]

to a dehydrative condensation to form a compound of a general formula [VI]

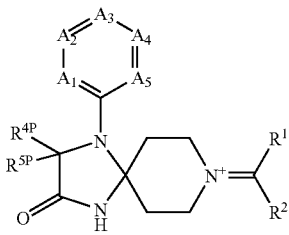

[VI]

[in which $R^1$, $R^2$, $R^{4P}$, $R^{5P}$, $A_1$, $A_2$, $A_3$, $A_4$ and $A_5$ have the earlier given significations];

2) a step of reducing the nitrogen-carbon double bond in the compound of above general formula [VI]; and 3) a step of removing the protective group(s), where the compound as obtained in 2) above has protective group(s).

The present invention furthermore relates to:

(17) use of the compounds or salts thereof as described in (1) for formulating pharmaceutical compositions adequate for analgesic purpose; relief from tolerance to narcotic analgesic represented by morphine; relief from dependence on narcotic analgesic represented by morphine; enhancing analgesic action, treating obesity; improving brain function; treating schizophrenia; treating regressive neurodegenerative diseases represented by Parkinsonism and chorea; antianxiety or antidepression; treating diabetes insipidus; treating polyuria; treating hypotension; anesthesia or assisting anesthesia; remedy for sleep disorders represented by insomnia including increased sleep latency, intermittent wakefulness and decreased sleep efficiency; remedy for circadian rhythm disorder such as jet lag; drug for improving erectile function; airway dilation during dyspenea such as asthma or antitussive; or as drug for ameliorating motility of digestive tract during hypokinesis of digestive tract.

(18) methods for pain-killing, relief from tolerance to narcotic analgesic represented by morphine; relief from dependence on narcotic analgesic represented by morphine; enhancing analgesic action, treating obesity; improving brain function; treating schizophrenia; treating regressive neurodegenerative diseases represented by Parkinsonism and chorea; antianxiety or antidepression; treating diabetes insipidus; treating polyuria; treating hypotension; anesthesia or assisting anesthesia; remedy for sleep disorders represented by insomnia including increased sleep latency, intermittent wakefulness and decreased sleep efficiency; remedy for circadian rhythm disorder such as jet lag; drug for improving erectile function; airway dilation during dyspenea such as asthma or antitussive; or as drug for ameliorating motility of digestive tract during hypokinesis of digestive tract, which are characterized by administering the compounds or salts thereof as described in (1) to patients: and

(19) a method for producing 4-oxoimidazolidine-2-spiropiperidine derivatives or salts thereof represented by a general formula [Ia]

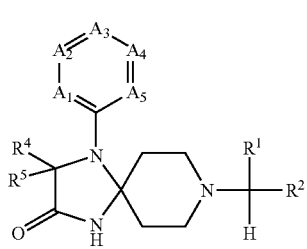

[Ia]

[in which $R^1$, $R^2$, $R^4$, $R^5$, $A_1$, $A_2$, $A_3$, $A_4$ and $A_5$ have the earlier given significations], which comprises 1) a step of subjecting a compound of a general formula [V]

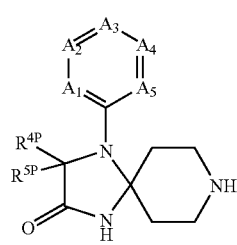

[V]

[in which $R^{4P}$, $R^{5P}$, $A_1$, $A_2$, $A_3$, $A_4$ and $A_5$ have the earlier given significations]

and a compound of a general formula [IV]

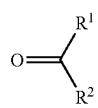

[IV]

[in which $R^1$ and $R^2$ have the earlier given significations]

to a reductive alkylation reaction in the presence of a reducing agent selected from a group consisting of sodium cyanoborohydride and sodium triacetoxyborohydride, and 2) a step of removing the protective group(s), where the compound as obtained in 1) above contains protective group(s).

Hereinafter the signs and terms used in the present specification are explained.

"Halogen" means fluorine, chlorine, bromine and iodine atoms.

"Lower alkyl" means $C_1$–$C_6$ alkyl groups, specific examples including methyl, ethyl, n-propyl, isopropyl, n-butyl, isobutyl, t-butyl, n-pentyl, isopentyl, neopentyl, tert-pentyl, 1-methylbutyl, 2-methylbutyl, 1,2-dimethylpropyl, 2,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl groups.

"Optionally hydroxyl- or amino-substituted lower alkyl" signifies, for example, those above-named lower alkyl groups whose optional one or more of hydrogen atom(s) is (are) substituted with hydroxyl and/or amino group(s), specific examples including, besides those lower alkyl groups, hydroxymethyl, 1-hydroxyethyl, 2-hydroxyethyl, 1-hydroxy-n-propyl, 2-hydroxy-n-propyl, 3-hydroxy-n-propyl, 1-hydroxy-isopropyl, 2-hydroxy-isopropyl, 3-hydroxy-n-butyl, 4-hydroxy-n-butyl, 1-hydroxyisobutyl, 3-hydroxy-isobutyl, 1-hydroxy-t-butyl, 5-hydroxy-n-pentyl and 6-hydroxy-n-hexyl groups, as hydroxyl-substituted lower alkyl.

Whereas, specific examples of amino-substituted lower alkyl include aminomethyl, 1-aminoethyl, 2-aminoethyl, 1-amino-n-propyl, 2-amino-n-propyl, 3-amino-n-propyl, 1-amino-isopropyl, 2-aminoisopropyl, 3-amino-n-butyl, 4-amino-n-butyl, 1-aminoisobutyl, 3-aminoisobutyl, 1-amino-t-butyl, 5-amino-n-pentyl and 6-amino-n-hexyl.

As examples of "$C_3$–$C_{12}$ aliphatic carbocyclic ring group", $C_3$–$C_{12}$ monocyclic or bicyclic aliphatic carbocyclic ring groups or $C_3$–$C_{12}$ spiro ring groups can be named, specific examples including such monocyclic aliphatic carbocyclic ring groups as cyclopropyl, cyclobutyl, cyclopentyl, cyclopentenyl, cyclohexyl, cyclohexenyl, cycloheptyl, cycloheptenyl, cyclooctyl, cyclooctenyl, cyclononyl, cyclodecyl, cycloundecyl and cyclododecyl; bicyclic aliphatic carbocyclic ring groups such as bicyclo[2.2.1]hepta-2-yl, bicyclo[3.1.1]hepta-3-yl, bicyclo[2.2.2]octa-2-yl, bicyclo [3.2.1]octa-1-yl, bicylo[3.2.1]octa-2-yl, bicyclo[3.2.1]octa-3-yl, bicyclo[3.2.1]octa-6-yl, bicyclo[3.2.1]octa-8-yl, bicyclo[3.2.2]nona-2-yl, bicyclo[3.2.2]nona-3-yl, bicyclo[3.3.1]nona-2-yl, bicyclo[3.3.1]nona-3-yl, bicyclo[3.3.1]nona-9-yl, bicyclo[4.2.1]nona-2-yl, bicyclo[4.2.1]nona-3-yl, bicyclo[4.3.0]nona-2-yl (hexahydroindan), bicyclo[4.3.0]nona-3-yl, bicyclo[3.3.2]deca-2-yl, bicyclo[3.3.2]deca-3-yl, bicyclo[4.2.2]deca-2-yl, bicyclo[4.2.2]deca-3-yl, bicyclo[4.3.1]deca-2-yl, bicyclo[4.3.1]deca-3-yl, decahydronaphthalene, bicyclo[3.3.3]undeca-2-yl, bicyclo[3.3.3]undeca-3-yl, bicyclo[4.3.2]undeca-2-yl, bicyclo[4.3.2]undeca-3-yl, bicyclo[4.3.2]undeca-7-yl and bicyclo[4.3.2]undeca-8-yl; and spiro ring groups such as spiro[2.4]hepta-4-yl, spiro[2.5]octa-4-yl, spiro[3.4]octa-5-yl, spiro[3.5]nona-5-yl, spiro[4.4]nona-6-yl, spiro[4.5]deca-1-yl, spiro[4.5]deca-6-yl, spiro[4.5]deca-7-yl, spiro[4.5]deca-8-yl, spiro[5.5]undeca-2-yl and spiro[5.5]undeca-3-yl.

As "salts" of the compounds represented by the general formula [I], pharmaceutically acceptable, customarily used salts are meant, examples of which including acid addition salts where the compounds contain amino group, or acid addition salts to the nitrogen in piperidine ring.

As the acid addition salts, for example, inorganic acid salts such as hydrochloride, sulfate, nitrate, phosphate and perchlorate; organic acid salts such as succinate, maleate, fumarate, tartarate, citrate, ascorbate and trifluoroacetate; and sulfonates such as methanesulfonate, isethionate, benzenesulfonate and p-toluenesulfonate can be named.

Compounds Represented by the General Formula [I]:

For still more concrete disclosure on the compounds represented by the general formula [I], those various symbols used in the general formula [I] are explained in further details, naming specific examples.

In the present invention, the position numbers in the compounds represented by the general formula [I] are assigned as in the following.

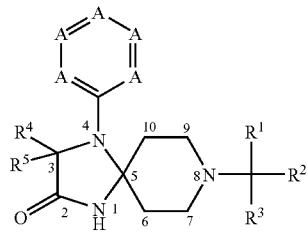

[I]

$A_1$, $A_2$, $A_3$, $A_4$ and $A_5$ each independently stands for optionally halogen-substituted methine or nitrogen.

As the substituent halogen, fluorine is preferred.

Where any of $A_1$, $A_2$, $A_3$, $A_4$ and $A_5$ is (are) nitrogen independently of each other, preferably only one of them is nitrogen and the rest are optionally halogen-substituted methine.

Preferably $A_1$, $A_2$, $A_3$, $A_4$ and $A_5$ are, independently of each other, optionally halogen-substituted methine groups, in particular, they all are unsubstituted methine groups.

$R^1$ and $R^2$ each independently stands for lower alkyl, or $R^1$ and $R^2$ may combine to form $C_3$–$C_{12}$ aliphatic carbocyclic ring group together with the carbon atom to which they bind. Examples of specific, preferred $R^1$ and $R^2$ include, independently of each other, methyl, ethyl, n-propyl, isopropyl, n-butyl, isobutyl, t-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylpropyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. Also where $R^1$ and $R^2$ combinedly form $C_3$–$C_{12}$ aliphatic carbocyclic ring group together with the carbon atom to which they bind, preferred examples include cyclopentyl, cyclohexyl, cycloheptyl, cyclooctyl and decahydronaphthalenyl groups.

In particular, as $R^1$ and $R^2$, methyl, ethyl, n-propyl, n-butyl, n-pentyl and 2,2-dimethylpropyl groups are recommended, and decahydronaphthalenyl group is recommended where $R^1$ and $R^2$ combinedly form $C_3$–$C_{12}$ aliphatic carbocyclic ring group together with the carbon atom to which they bind.

As $R^3$, hydrogen or those lower alkyl groups which are named as specific examples of $R^1$ can be named, in particular, hydrogen, methyl, ethyl and n-propyl being recommended.

As preferred combination of $R^1$, $R^2$ and $R^3$,
$R^1$=methyl, $R^2$=n-butyl, $R^3$=H,
$R^1$=methyl, $R^2$=methyl, $R^3$=n-butyl,
$R^1$=methyl, $R^2$=2,2-dimethylpropyl, $R^3$=H,
$R^1$=methyl, $R^2$=methyl, $R^3$=2,2-dimethylpropyl,
$R^1$=ethyl, $R^2$=n-butyl, $R^3$=H,
$R^1$=ethyl, $R^2$=2,2-dimethylpropyl, $R^3$=H,
$R^1$=ethyl, $R^2$=n-butyl, $R^3$=metyl,
$R^1$=ethyl, $R^2$=2,2-dimethylpropyl, $R^3$=methyl, and
$R^1$ and $R^2$ combinedly form decahydronaphthalene together with the carbon atom to which they bind, $R^3$=H, are recommended. Here the substituents on $R^1$ and $R^2$ may be interchanged, where $R^3$ is H. Also when $R^3$ is other than hydrogen, the substituents on $R^1$, $R^2$ and $R^3$ may be interchanged among one another.

$R^4$ and $R^5$ each independently stands for hydrogen or optionally hydroxyl- or amino-substituted lower alkyl.

Preferred examples of hydroxyl-substituted lower alkyl include hydroxymethyl, 1-hydroxyethyl, 2-hydroxyethyl, 1-hydroxy-n-propyl, 2-hydroxy-n-propyl, 3-hydroxy-n-propyl, 4-hydroxy-n-butyl, 5-hydroxy-n-pentyl and 6-hydroxy-n-hexyl, in particular, hydroxymethyl, 2-hydroxyethyl and 3-hydroxy-n-propyl being recommended.

Preferred examples of amino-substituted lower alkyl include aminomethyl, 1-aminoethyl, 2-aminoethyl, 1-amino-n-propyl, 2-amino-n-propyl, 3-amino-n-propyl, 4-amino-n-butyl, 5-amino-n-pentyl and 6-amino-n-hexyl, in particular, aminomethyl, 2-aminoethyl and 3-amino-n-propyl being recommended.

Hydrogen or hydroxyl-substituted lower alkyl are especially recommendable as $R^4$ or $R^5$.

As combinations of $R^4$ and $R^5$, those particularly preferred are:
$R^4$=H, $R^5$=H,
$R^4$=H, $R^5$=hydroxymethyl, and
$R^4$=H, $R^5$=2-hydroxyethyl.

Here the substituents on $R^4$ and $R^5$ may be interchanged.

As specific compounds represented by the general formula [I],
4-(3-fluorophenyl)-3-(2-hydroxyethyl)-8-(1,1,3,3-tetramethylbutyl)-1,4,8-triazaspiro[4.5]decan-2-one,
4-(3-fluorophenyl)-(3S or 3R)-3-(2-hydroxyethyl)-8-(1,1,3,3-tetramethylbutyl)-1,4,8-triazaspiro[4.5]decan-2-one,
4-(3-fluorophenyl)-8-(1,1,3,3-tetramethylbutyl)-1,4,8-triazaspiro[4.5]decan-2-one,
4-phenyl-8-(1,1,3,3-tetramethylbutyl)-1,4,8-triazaspiro[4.5]decan-2-one,
4-phenyl-8-(1-ethylpentyl)-1,4,8-triazaspiro[4.5]decan-2-one, and
8-decahydronaphthalen-2-yl-4-phenyl-1,4,8-triazaspiro[4.5]decan-2-one are named for example. Of these, particularly
4-(3-fluorophenyl)-(3S)-3-(2-hydroxyethyl)-8-(1,1,3,3-tetramethylbutyl)-1,4,8-triazaspiro[4.5]decan-2-one,
4-(3-fluorophenyl)-(3R)-3-(2-hydroxyethyl)-8-(1,1,3,3-tetramethylbutyl)-1,4,8-triazaspiro[4.5]decan-2-one,
4-phenyl-8-(1,1,3,3-tetramethylbutyl)-1,4,8-triazaspiro[4.5]decan-2-one are recommended.

Production Methods of the Compounds Represented by the General Formula [I]

Those compounds represented by the general formula [I] can be produced, for example, by the following methods.

Production Method 1

The compounds represented by the general formula [I] can be obtained by 1) a step of subjecting a compound of the general formula [II]

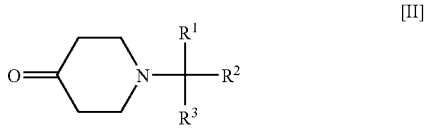

[in which $R^1$, $R^2$ and $R^3$ have the earlier given significations] and a compound of the general formula [III]

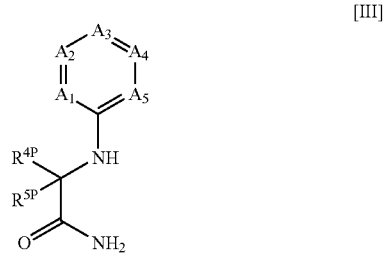

[in which $R^{4P}$, $R^{5P}$, $A_1$, $A_2$, $A_3$, $A_4$ and $A_5$ have the earlier given significations]

to dehydrative condensation, preferably in the presence of an acid; and 2) a step of removing the protective group(s), where the compound as obtained in 1) above contains protective group(s).

Where $R^4$ and/or $R^5$ in the compounds represented by the general formula [I] contain amino groups or hydroxyl groups which do not participate in the reaction, said amino groups or hydroxyl groups may be suitably protected with amino-protective groups or hydroxyl-protective groups to convert them to $R^{4P}$ and/or $R^{5P}$ before conducting the reaction, which protective groups can be removed after the reaction to convert them back to $R^4$ and/or $R^5$.

As the amino-protective groups, aralkyl such as benzyl, p-methoxybenzyl, 3,4-dimethoxybenzyl, o-nitrobenzyl, p-nitrobenzyl, benzhydryl and trityl; lower alkanoyl such as formyl, acetyl, propionyl, butyryl, pivaloyl; benzoyl; arylalkanoyl such as phenylacetyl and phenoxyacetyl; lower alkoxy carbonyl such as methoxycarbonyl, ethoxycarbonyl and propyloxycarbonyl; aralkyloxycarbonyl such as benzyloxycarbonyl, p-nitrobenzyloxycarbonyl and phenethyloxycarbonyl; phthaloyl; and aralkylidene such as benzylidene, p-chlorobenzylidene and o-nitrobenzylidene can be named for example, preferably benzyl, benzyloxycarbonyl and trityl being recommended.

As the hydroxyl-protective groups, substituted silyl such as tert-butyldimethylsilyl and tert-butyldiphenylsilyl; lower alkoxymethyl such as methoxymethyl and 2-methoxyethoxymethyl; tetrahydropyranyl; trimethylsilylethoxymethyl; aralkyl such as benzyl, p-methoxybenzyl, 2,3-dimethoxybenzyl, o-nitrobenzyl, p-nitrobenzyl and trityl; and acyl such as formyl and acetyl can be named for example, preferably benzyl, tert-butyldiphenylsilyl and acetyl being recommended.

Methods of introducing such protective groups differ depending on the kind of protective group and stability of object individual compound represented by the general formula [I]. The introduction can be conducted, for example, by methods described in literature, *Protective Groups in Organic Synthesis*, T. W. Greene, John Wiley & Sons (1981) (which is hereafter referred to as "literature P") or methods corresponding thereto.

The reaction of a compound of the general formula [II] with a compound of the general formula [III] is conducted using equimolar amounts of the compounds of the general formulae [II] and [III] or using either one of the compound in slight molar excess than the other, preferably in the presence of an acid and normally in an inert solvent which has no detrimental effect on the reaction.

As the inert solvent, benzene, toluene, xylene, chloroform, dichloroethane, chlorobenzene and the like can be named for example.

As the acid, for example, sulfonic acid such as camphorsulfonic acid, benzenesulfonic acid, p-toluenesulfonic acid, methanesulfonic acid and ethanesulfonic acid; and Lewis acid such as boron trifluoride, titanium tetrachloride, tetraalkyl ($C_1$–$C_8$) titanate, tin chloride, zinc chloride, aluminum chloride, trialkyl ($C_1$–$C_4$) aluminum, trialkoxy ($C_1$–$C_4$) silane and trimethylsilyltrifluoromethane sulfonate can be named, preferably camphorsulfonic acid being recommended.

As the use rate of such an acid, it may range 20–300, preferably 100–200, parts by weight per 100 parts by weight of the sum of the compounds of the general formulae [II] and [III].

As the reaction temperature, normally it may range 60–150° C., preferably 100–130° C. being recommended. As the reaction time, normally it may range from an hour to 3 days, preferably 3–24 hours being recommended.

After completion of the reaction, the reaction product is processed as it is in ordinary manner where it does not contain protective group(s), or where it contains protective group(s), the protective group(s) are removed before the ordinary processing, to provide crude product of the compound represented by the general formula [I].

Removal of the protective group(s) can be conducted by differing methods depending on the kind of the protective group(s) to be removed and stability of the compound represented by the general formula [I]. For example, the removal is conducted following those methods described in literature P or those corresponding thereto, e.g., by solvolysis using base, i.e., having equimolar to a large excess of base, preferably potassium hydroxide or calcium hydroxide, act on the reaction product; or by chemical reduction using metal hydride complex or catalytic reduction using palladium-on-carbon catalyst, palladium hydroxide-on-carbon catalyst, palladium hydroxide, Raney nickel catalyst or the like.

The compounds of the general formula [II] or [III] may be those available in the market, or can be prepared by known methods, or the following production methods A–D, or those as described in Examples, in suitable combination.

Production method A

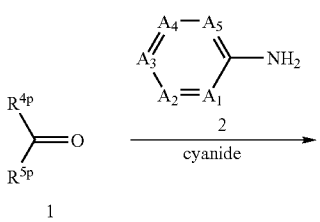

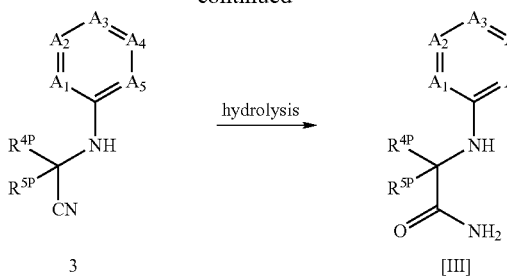

[in which $R^{4P}$, $R^{5P}$, $A_1$, $A_2$, $A_3$, $A_4$ and $A_5$ have the earlier given significations].

This production method is for producing the compounds represented by the general formula [III]. According to this method, compound 2 is caused to act on compound 1 in the presence of cyanide to form compound 3, and then the cyano group in compound 3 is hydrolyzed to produce a compound of the general formula [III].

The step of producing compound 3 from compound 1 can be conducted by, for example, having compound 2 and a cyanide such as trimethylsilylnitrile, potassium cyanide, sodium cyanide or the like act on compound 1 in the absence of any solvent or in the presence of a solvent such as acetic acid, water, methanol, ethanol, dioxane or a mixture thereof.

As the use rates of compound 2 and the cyanide, for example, 1–5 moles of compound 2 and 1–5 moles of cyanide per mole of compound 1 can be used, preferably 1–2 moles of both per mole of compound 1 being recommended.

The reaction temperature may normally range from 0° C. to the boiling point of the solvent used for the reaction, preferably 0–30° C. being recommended.

The reaction time may normally range from 1 hour to 3 days, preferably 2–24 hours being recommended. Said reaction can also be conducted in the presence of Lewis acid where necessary, examples of useful Lewis acid including ytterbium (III) trifluoromethanesulfonate, boron trifluoride and zinc chloride.

Exemplary use rate of such Lewis acid ranges 0.1–100, preferably 0.1–10, parts by weight per 100 parts by weight of the sum of compounds 1 and 2.

The step of producing a compound of the general formula [III] from compound 3 can be conducted by, for example, having an acid such as conc. sulfuric acid, conc. hydrochloric acid, phosphoric acid or the like act on compound 3 in an alcoholic solvent such as methanol or ethanol to hydrolyze the cyano group.

Exemplary use rate of the acid may range 100–1,000, preferably 100–500, parts by weight per 100 parts by weight of compound 3.

Exemplary reaction temperature may normally range 0–100° C., preferably 0°–30° C. being recommended.

Exemplary reaction time may normally range 1–24 hours, preferably 1–8 hours being recommended.

The compounds represented by the general formula [III] can also be obtained by a method of hydrolyzing compound 3 using an inorganic base in, for example, an alcoholic solvent such as methanol or ethanol, in the presence of hydrogen peroxide.

In such a reaction, the reaction temperature may normally range from 0° C. to the boiling point of the solvent used for the reaction, preferably 0–30° C. being recommended.

As the reaction time, it may range 1–24 hours, for example, preferably 2–10 hours being recommended.

Examples of useful inorganic base include lithium hydroxide, sodium hydroxide, potassium hydroxide, potassium carbonate, sodium carbonate and the like.

The use rate of the inorganic base may range from 2 moles to molar excess, preferably 2–3 moles, per mole of compound 3.

The use rate of hydrogen peroxide may range from 1.1 moles to molar excess, preferably 2–4 moles, per mole of compound 3.

Compounds 1 or 2 may be those available in the market, or they can be prepared by known methods, methods described in Examples or those corresponding thereto, in suitable combination.

Production method B

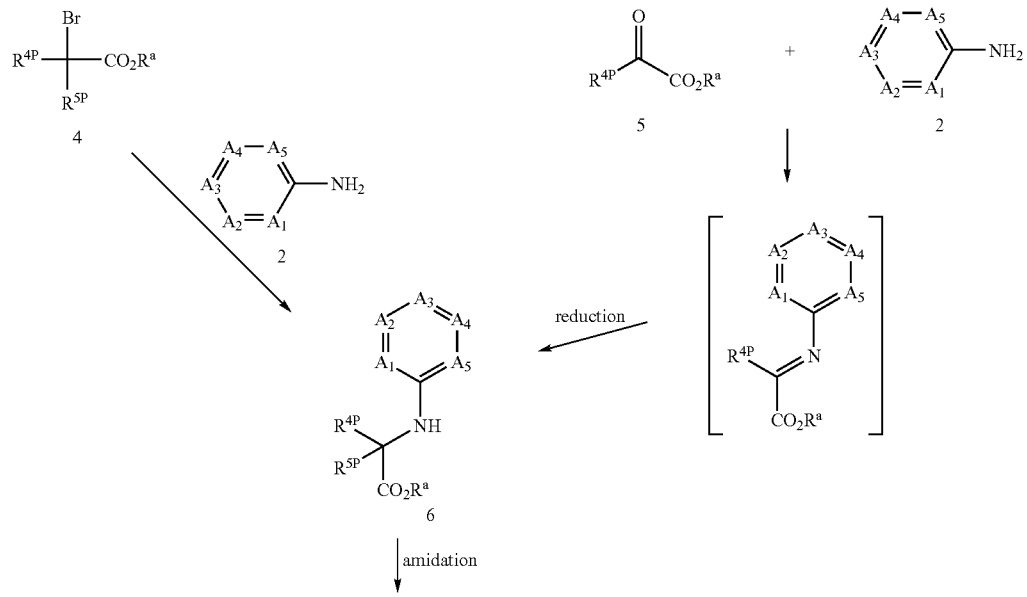

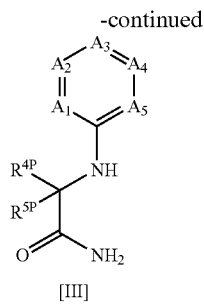

[III]

[in the above formulae, $R^a$ stands for lower alkyl such as methyl, ethyl, propyl or the like, and $R^{4P}$, $R^{5P}$, $A_1$, $A_2$, $A_3$, $A_4$ and $A_5$ have the earlier given significations].

This method is for producing the compounds of the general formula [III]. According to this method, compound 2 is caused to act on compound 4 to convert the latter to compound 6, and then the ester group in the compound 6 is converted to amido group to provide a compound represented by the general formula [III].

Said compound 6 may also be produced by reacting compound 5 with compound 2 to form an imine intermediate and then reducing the imine intermediate (in which case $R^{5P}$ becomes H).

The step of forming compound 6 from compound 4 can be conducted by, for example, acting compound 2 on compound 4 in a solvent like benzene, toluene, acetonitrile, dioxane, dimethylfomamide or mixtures thereof.

Use rate of compound 2 may range 1–5 moles, preferably 1–2 moles, per mole of compound 4.

The reaction temperature may normally range from 0° to boiling point of individual solvent used for the reaction, preferably from room temperature to boiling point of said solvent.

Reaction time may normally range 1–24 hours, preferably 3–15 hours being recommended.

The above reaction may also be conducted in the presence of base, where necessary. Examples of useful base include organic base such as triethylamine, diisopropylethylamine, pyridine and 4-dimethylaminopyridine; and inorganic base such as sodium carbonate, potassium carbonate and sodium hydrogencarbonate.

Use rate of such a base may range from 2 moles to a molar excess, preferably 2–3 moles, per mole of compound 4.

The step of producing a compound of the general formula [III] from compound 6 can be conducted by, for example, having excessive aqueous ammonia act on compound 6 in water, methanol, ethanol, dioxane, toluene or their mixture.

Reaction temperature may normally range from 0° C. to boiling point of individual solvent used for the reaction, preferably 0–30° C. being recommended.

Reaction time may normally range from 1 hour to 2 days, preferably 1–8 hours being recommended.

The step of producing compound 6 from compound 5 can be conducted by, for example, having compound 2 act on compound 5 in a solvent such as toluene, benzene or the like in the presence of a catalytic amount of an acid such as camphorsulfonic acid or toluenesulfonic acid, to form an imine intermediate, and then reducing the imine intermediate as it is or after isolating the intermediate.

Use rate of the compound 2 may range 1–10 moles, preferably 1–2 moles, per mole of the compound 5.

The reaction temperature in the occasion of producing the imine intermediate preferably is boiling point of the solvent used for the reaction, and it is preferred to eliminate the formed water by means of, e.g., Dean-Stark water separator.

Reaction time may normally range from 1 hour to 3 days, preferably 5–15 hours being recommended.

Reduction of the imine intermediate can be conducted by, for example, reducing reaction using metal hydride complex such as lithium borohydride, sodium borohydride, sodium cyanoborohydride, sodium triacetoxyborohydride, lithium aluminum hydride and the like; or catalytic reduction using palladium hydroxide-on-carbon, palladium-on-carbon, Raney-nickel catalyst and the like.

In the reducing reaction using metal hydride complex, use rate of the reducing agent may normally range 1 mole to molar excess, preferably 1–5 moles, per mole of the imine intermediate.

In said reducing reaction, depending on the kind of reducing agent, suitable solvent may be used, examples of useful solvent including alcohols such as methanol, ethanol and the like; ethers such as dimethyl ether, ethyl ether, diisopropyl ether, dibutyl ether, dimethoxyethane, dioxane, tetrahydrofuran, diglyme and the like; halogenated hydrocarbons such as methylene chloride, chloroform, dichloroethane and the like; aliphatic hydrocarbons such as pentane, hexane, heptane, cyclohexane and the like; aromatic hydrocarbons such as benzene, toluene and the like; or mixed solvents of the foregoing.

The reaction temperature may normally range −20–100° C., preferably 0–30° C. being recommended.

The reaction time may normally range 5 minutes–7 days, preferably 1–6 hours being recommended.

As the hydrogen pressure in the catalytic reducing reaction, it may normally be from atmospheric to 5 atmospheres. The use rate of the catalyst may normally range 1–100 parts by weight, preferably 1–10 parts by weight, per 100 parts by weight of compound 5.

Commercial compound 4 or compound 5 can be used, or they may be produced by known methods, methods as described in Examples or those corresponding thereto, in suitable combination where necessary.

Production method C

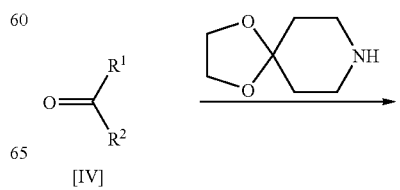

[IV]

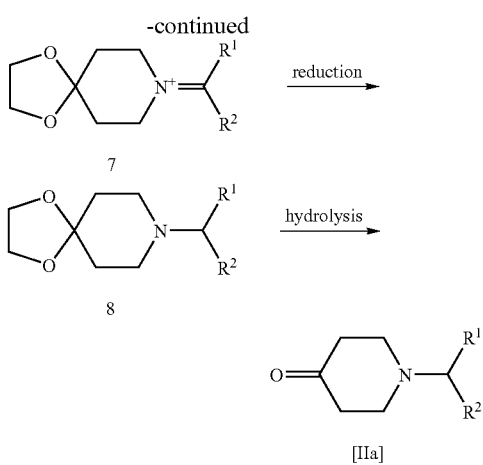

[in the formulae, $R^1$ and $R^2$ have the earlier given significations]

This production method is for producing the compounds represented by the general formula [IIa] (i.e., the compounds of the general formula [II] whose $R^3$=H). According to this method, compounds of the general formula [IIa] can be obtained by reacting a compound of the general formula [IV] with 1,4-dioxa-8-azaspiro[4.5]decane to form a compound 7, then reducing said compound 7 to compound 8, and hydrolyzing ketal in said compound 8.

The reaction of a compound of the general formula [IV] with 1,4-dioxa-8-azaspiro[4.5]decane is normally conducted using a slight molar excess of 1,4-dioxa-8-azaspiro[4.5]decane.

The reaction is normally conducted in an inert solvent, examples of the inert solvent including alcohols such as methanol, ethanol, propanol and the like; ethers such as ethyl ether, tetrahydrofuran, dioxane and the like; halogenated hydrocarbons such as methylene chloride, chloroform, dichloroethane and the like; aromatic hydrocarbons such as benzene, toluene, chlorobenzene xylene and the like; aprotic polar solvents such as dimethylformamide, acetonitrile, hexamethylphosphoric triamide, or mixtures of the foregoing.

The reaction temperature may normally range from 0° C. to the boiling point of the solvent used for the reaction, preferably 20–100° C. being recommended.

The reaction time may normally range from 5 minutes to 48 hours, preferably 10 minutes to 24 hours being recommended.

After termination of the above reaction, the reaction liquid may be used in the reducing reaction in the next step as it is, or it may be distilled off, or the compound 7 may be isolated therefrom by ordinary separation means, to be subjected to the subsequent reducing reaction.

Said reducing reaction can be conducted by, for example, reducing reaction using metal hydride complex such as lithium borohydride, sodium borohydride, sodium cyanoborohydride, sodium triacetoxyborohydride, lithium aluminum hydride and the like; or catalytic reduction using palladium hydroxide-on-carbon, palladium-on-carbon, Raney-nickel catalyst and the like.

In particular, when a reducing agent which predominantly reduces imine, such as sodium cyanoborohydride or sodium triacetoxyborohydride, is used, it is unnecessary to isolate compound 7 in advance of the reduction.

Where a metal hydride complex is used as the reducing agent, use rate of the reducing agent normally can be, for example, 1 mole to molar excess, preferably 1–5 moles, per mole of compound 7.

In said reducing reaction, depending on the kind of reducing agent, suitable solvent may be used, examples of useful solvent including alcohols such as methanol, ethanol and the like; ethers such as dimethyl ether, ethyl ether, diisopropyl ether, dibutyl ether, dimethoxyethane, dioxane, tetrahydrofuran, diglyme and the like; halogenated hydrocarbons such as methylene chloride, chloroform, dichloroethane and the like; aliphatic hydrocarbons such as pentane, hexane, heptane, cyclohexane and the like; aromatic hydrocarbons such as benzene, toluene and the like; or mixed solvents of the foregoing.

The reaction temperature may normally range –20–100° C., preferably 0–30° C. being recommended.

The reaction time may normally range 5 minutes–7 days, preferably 1–6 hours being recommended.

As the hydrogen pressure in the catalytic reducing reaction, it may normally range from atmospheric to 5 atmospheres. The use rate of the catalyst may normally range 1–100 parts by weight, preferably 1–10 parts by weight, per 100 parts by weight of compound 7.

The step of producing compounds of the general formula [II] from compound 8 can be conducted by, for example, having an excessive amount of an acid such as hydrochloric acid, sulfuric acid, p-toluenesulfonic acid, acetic acid, oxalic acid and the like act on compound 8 in a solvent such as tetrahydrofuran, acetone, water and the like.

The reaction temperature may normally range from 0° C. to the boiling point of individual solvent used for the reaction, preferably from room temperature to the boiling point of the solvent used for the reaction being recommended.

The reaction time may normally ranges 1–24 hours, preferably 1–8 hours being recommended.

Incidentally, compounds represented by the general formula [IV] may be commercial products in general, or can be prepared by known methods (e.g., those described in Comprehensive Organic Transformation, second ed., ed. by Richard C, Larock, Wiley-VCH, 1999, 1205–1261) or methods corresponding thereto, in suitable combination where necessary.

Production method D

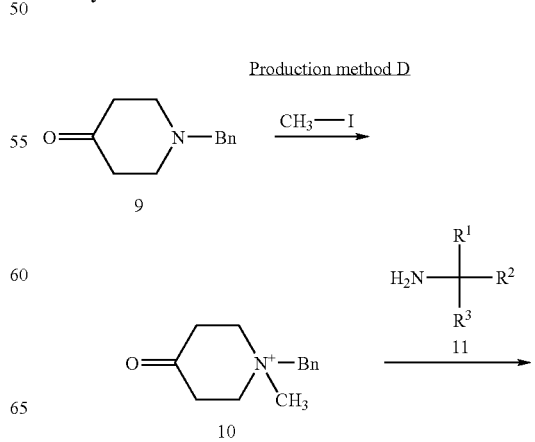

-continued

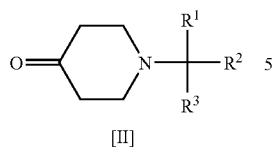

[II]

[in which Bn stands for benzyl group; and $R^1$, $R^2$ and $R^3$ have the earlier given significations].

This method is an effective production method also in case $R^1$, $R^2$ and $R^3$ in the compounds of the general formula [III] are alkyl, which can be conducted following the method as described in JP 2000-128879A. That is, the method comprises reacting commercial benzylpiperidone 9 with methyl iodide to form a compound 10, and thereafter reacting said compound 10 with a compound 11 in the presence of an inorganic base to form a compound of the general formula [II].

In the reaction of said compound 10 with compound 11, use rate of the compound 11 may range 0.9–1.5 moles, preferably 1.1–1.2 moles, per mole of the compound 10.

Examples of useful inorganic base include lithium carbonate, sodium carbonate, potassium carbonate and the like, and its use rate may ranges 1.0–2.0 moles, preferably 1.2–1.5 moles, per mole of the compound 10.

The reaction temperature may range 20–150° C., preferably 50–120° C. being recommended.

The reaction is conducted in a reaction solvent and as specific reaction solvent, for example, lower alcohol such as methanol, ethanol and the like can be used.

Compound 11 may be a commercial product, or can be prepared by those methods described in *Organic Synthesis IV*, 910; *J. Med. Chem.*, 1981, 24, 1429; and *Org. React.*, 1969, 17, 313.

Production method 2

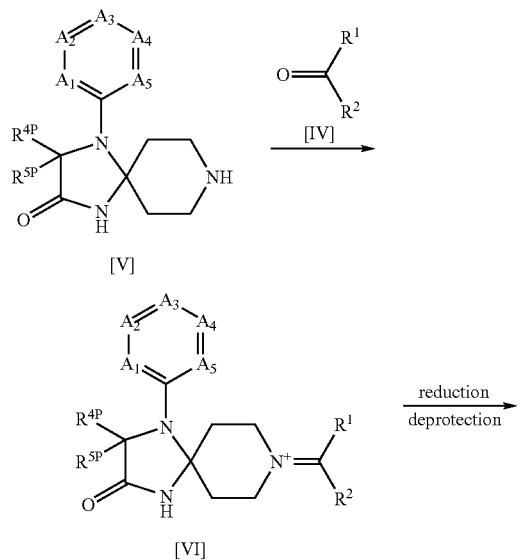

-continued

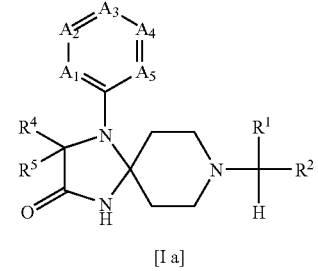

[Ia]

[in the formulae, $R^1$, $R^2$, $R^4$, $R^5$, $R^{4P}$, $R^{5P}$, $A_1$, $A_2$, $A_3$, $A_4$ and $A_5$ have the earlier given significations].

This production method 2 is for producing compounds represented by the general formula [Ia], which comprises:
2-1) a step of subjecting a compound of the general formula [V] and a compound of the general formula [IV] to dehydrative condensation to form a compound of the general formula [VI];
2-2) a step of reducing the nitrogen-carbon double bond in the compound of the general formula [VI], and
2-3) a step of removing protective group(s), where the compound as obtained in above step 2-2) has protective group(s).

The condensation reaction of a compound of the general formula [V] with a compound of the general formula [IV] is normally conducted by using the two in equimolar amouonts or using either one of them in slight molar excess, and mixing them by stirring.

The reaction is normally conducted in an inert solvent, examples of the inert solvent including alcohols such as methanol, ethanol, propanol, 2-propanol and the like; ethers such as ethyl ether, tetrahydrofuran, dioxane and the like; halogenated hydrocarbons such as methylene chloride, chloroform, 1,2-dichloroethane and the like; aromatic hydrocarbons such as benzene, toluene, chlorobenzene, xylene and the like; aprotic polar solvents such as dimethylformamide, acetonitrile, hexamethylphosphoric triamide, or mixtures of the foregoing.

The reaction temperature may normally range from 0° C. to the boiling point of the solvent used for the reaction, preferably 20–100° C. being recommended.

The reaction time may normally range from 5 minutes to 48 hours, preferably 10 minutes to 24 hours being recommended.

Reduction of compounds of the general formula [VI] can be conducted by, for example, reducing reaction using metal hydride complex such as lithium borohydride, sodium borohydride, sodium cyanoborohydride, sodium triacetoxyborohydride, lithium aluminum hydride and the like; or catalytic reduction using palladium-on-carbon, Raney-nickel catalyst and the like.

As the solvent useful in this reducing reaction, same solvents to those useful in the above condensation reaction can be applied. The compound of the general formula [VI] as obtained in the condensation reaction may be isolated and subjected to this reducing reaction, or the reaction liquid after the condensation reaction can be subjected to this reducing reaction as it is.

In particular, when a reducing agent which predominantly reduces imine-enamine, such as sodium cyanoborohydride or sodium triacetoxyborohydride, is used, it is unnecessary to isolate the compound of the general formula [VI] in advance of the reduction. Furthermore, by conducting the condensation reaction in the presence of such a reducing agent which predominantly reduces imine-enamine, the object product can be obtained in one pot (which reaction may hereafter be referred to as "reductive alkylation reaction").

Where a metal hydride complex is used as the reducing agent, use rate of the reducing agent may normally range from 1 mole to molar excess, preferably 1–5 moles, per mole of the compound of the general formula [VI].

The reaction temperature normally may range $-20$–$100°$ C., preferably 0–30° C. being recommended.

The reaction time may normally range 5 minutes–7 days, preferably 1–6 hours being recommended.

As the hydrogen pressure in the catalytic reducing reaction, it may normally range from atmospheric to 5 atmospheres. The use rate of the catalyst may normally range 1–100 parts by weight, preferably 1–10 parts by weight, per 100 parts by weight of the compound of the general formula [VI].

When the product contains protective group(s) after the reaction is completed, the protective group(s) is (are) removed by such methods as described in "literature P", to provide a crude product of the compound represented by the general formula [Ia].

As the compounds represented by the general formula [V], those described in International Publication WO 00/34280 pamphlet can be used, or they can be prepared by reacting compounds represented by the general formula [III] with commercially available Boc-piperidone following the production method 1 and then removing the Boc group.

Crude products of the compounds represented by the general formula [I] or [Ia] can be purified by heretofore known methods.

The purification can be accomplished by such separation means as column chromatography using an adsorbing resin like silica gel, alumina or the like or ion-exchange resin, preparative thin layer chromatography, high-performance liquid chromatography, solvent extraction, or recrystallization, reprecipitation and the like, either singly or in suitable combination.

Furthermore, where the compounds of the general formula [I] are racemates, they can be separated by the means following known methods, for example, separation with optically active column, recrystallization, crystallization using an optical resolution agent, or the like.

The compounds represented by the general formula [I] of the present invention are in occasions present in the forms of their stereoisomers such as optical isomers, diastereoisomers or geometrical isomers, depending on configuration of substituents thereon. The compounds of the general formula [I] of the present invention encompass all of those stereoisomers and their mixtures. Moreover, various crystals, hydrates or solvates of the compounds of the present invention also belong to the scope of the present invention.

Pharmacological Activities of the Compounds Represented by the General Formula [I]

Utility of the compounds of this invention as medicine is verified, for example, by the following pharmacological tests.

Pharmacological Test 1 (Nociceptin Receptor Binding Assay)

cDNA which codes a human nociceptin receptor gene was cloned into an expression vector pCR3 (Invitrogen) to prepare pCR3/ORL1. Next, pCR3/ORL1 was transfected in CHO cells using a transfectam (Nippongene) to obtain a stable expression strain (CHO/ORL1 cells) having resistance against 1 mg/ml G418. Membrane fractions were prepared from this stable expression strain to carry out a receptor binding assay.

The membrane of 11 μg, 50 pM [$^{125}$I] Tyr$^{14}$-Nociceptin (Amersham), 1 mg Wheatgerm agglutinin SPA beads (PVT based; Amersham) and each test compound were suspended in an NC buffer (50 mM Hepes, 10 mM sodium chloride, 1 mM magnesium chloride, 2.5 mM calcium chloride, 0.1% BSA, 0.025% bacitracin, pH 7.4) and incubated at 37° C. for 60 minutes, and then the radioactivity was determined. The binding activity to the nociceptin receptor was indicated by the 50% inhibition concentration ($IC_{50}$ value) of [$^{125}$I] Tyr$^{14}$-Nociceptin binding by each compound of the present invention at various concentrations. The results were as shown in Table 1. Less numerical values indicate stronger tendency of the tested compounds to bind to the receptor.

TABLE 1

| Test Compound | $IC_{50}$(nM) |
| --- | --- |
| Example 1 (3S*) | 0.49 |
| Example 1 (3R*) | 1.20 |
| Example 2 | 0.20 |
| Example 3 | 0.27 |
| Example 4 | 2.20 |
| Example 5 | 0.35 |

Pharmacological Test 2 (Activity on Nociceptin-Elicited G Protein Activation)

CHO cells which stably expressed a nociceptin receptor ORL1 were used to investigate the action of each test compound on nociceptin-elicited G protein activation. A membrane prepared from the CHO/ORL1 cells, 50 nM nociceptin, 200 pM GTPγ[$^{35}$S] (NEN), 1.5 mg Wheatgerm agglutinin SPA beads (PVT based; Amersham) and each of the test compounds were mixed in a GDP buffer (20 mM Hepes, 100 mM sodium chloride, 10 mM magnesium chloride, 1 mM EDTA, 5 μM GDP, pH 7.4) and incubated at 25° C. for 150 minutes, and then the radioactivity was determined. The G protein activation by the compounds of the present invention were determined by comparing the increase in GTPγ [$^{35}$S] binding caused by the compounds of the present invention at various concentrations with the increase caused by 1 μM of nociceptin, and indicated by their concentration values eliciting the 50% activation ($EC_{50}$ values). The results were as shown in Table 2, which demonstrate that the compounds of the present invention possess nociceptin receptor agonist activity.

TABLE 2

| Test Compound | $EC_{50}$(nM) |
| --- | --- |
| Example 1 (3S*) | 3.0 |
| Example 1 (3R*) | 4.4 |
| Example 2 | 1.2 |
| Example 3 | 3.5 |
| Example 4 | 89.0 |
| Example 5 | 3.8 |

From the above, the compounds represented by the general formula [I] are found to act as agonist of nociceptin receptor and useful as analgesic, reliever from tolerance to narcotic analgesic represented by morphine; reliever from dependence on narcotic analgesic represented by morphine; analgesic enhancer; antiobestic; drug for ameliorating brain function; remedy for schizophrenia; drug for treating regressive neurodegenerative diseases represented by Parkinsonism and chorea; antianxiety agent or antidepressant; remedy for diabetes insipidus; remedy for polyuria; remedy for hypotension; anesthetic or anesthetic adminiculum; remedy for sleep disorders represented by insomnia including increased sleep latency, intermittent wakefulness and decreased sleep efficiency; remedy for circadian rhythm disorder such as jet lag; drug for improving erectile function; airway dilation during dyspenea such as asthma or antitussive; or as drug for ameliorating motility of digestive tract during hypokinesis of digestive tract.

Furthermore, because the compounds represented by the general formula [I] possess agonistic activity on nociceptin receptor, they can be used, besides their use as nociceptin receptor agonist, as index compounds in the occasion of, for example, screening agonist or antagonist activities.

Pharmaceutical Compositions Containing the Compounds Represented by the General Formula [I]

The compounds of the present invention can be administered orally or parenterally and, as formulated into preparation forms suitable for such administration routes, can be used as analgesic, reliever from tolerance to narcotic analgesic represented by morphine; reliever from dependence on narcotic analgesic represented by morphine; analgesic enhancer; antiobestic; drug for ameliorating brain function; remedy for schizophrenia; drug for treating regressive neurodegenerative diseases represented by Parkinsonism and chorea; antianxiety agent or antidepressant; remedy for diabetes insipidus; remedy for polyuria; remedy for hypotension; anesthetic or anesthetic adminiculum; remedy for sleep disorders represented by insomnia including increased sleep latency, intermittent wakefulness and decreased sleep efficiency; remedy for circadian rhythm disorder such as jet lag; drug for improving erectile function; airway dilation during dyspenea such as asthma or antitussive; or as drug for ameliorating motility of digestive tract during hypokinesis of digestive tract.

In clinically using the compounds of the present invention, they can be formulated into various preparation forms suitable for individual mode of administration, with pharmaceutically acceptable carriers. As the carriers, various additives customarily used in the field of medical preparations can be used, examples of which including gelatin, lactose, glucose, sucrose, starch, corn starch, partial α-starch, crystalline cellulose, methyl cellulose, ethyl cellulose, hydroxypropyl cellulose, hydroxypropylmethyl cellulose, carboxymethyl cellulose, citric acid, trisodium citrate, sorbitol, sorbitan fatty acid ester, polysorbate, sucrose fatty acid ester, polyoxyethylene fatty acid ester, stearic acid, calcium stearate, magnesium stearate, light silicic anhydride, talc, titanium dioxide, magnesium aluminate metasilicate, calcium carbonate, anhydrous calcium phosphate, calcium sulfate, microcrystalline wax, white petrolatum, lanolin, vaseline, vegetable oil, hardened castor oil, cetyl alcohol, stearyl alcohol, benzyl alcohol, acacia, propylene glycol, polyvinyl alcohol, polyvinylpyrrolidone, polyalkylene glycol such as polyethylene glycol or polypropylene glycol, cyclodextrin or hydroxypropyl cyclodextrin, ethanol, glycerine and water.

As the preparation forms formulated as mixtures of these carriers with the compounds of the present invention, solid preparations such as tablets, capsules, granules, powders and suppositories; liquid preparations such as syrups, elixirs and injections can be named. These preparations can be formulated according to conventional methods used in the field of pharmaceutical preparations. Liquid preparations may be in a form which is dissolved or suspended in water or other suitable medium immediately prior to use. In particular, injections may be in the form of a solution or suspension in physiological saline solution or a glucose solution, to which a buffer agent, a preservative or the like may be added.

These preparations may contain a compound(s) of the present invention at the ratios of 1.0–99.9 wt %, preferably 1.0–60 wt %, based on the total pharmaceutical composition and also pharmaceutically acceptable carrier(s), at a ratio of 0.1–99.0 wt %, preferably 40–99.0 wt %. These preparations may further contain other therapeutically active compounds.

Where the compounds of the present invention are used as analgesic, reliever from tolerance to narcotic analgesic represented by morphine; reliever from dependence on narcotic analgesic represented by morphine; analgesic enhancer; antiobestic; drug for ameliorating brain function; remedy for schizophrenia; drug for treating regressive neurodegenerative diseases represented by Parkinsonism and chorea; antianxiety agent or antidepressant; remedy for diabetes insipidus; remedy for polyuria; remedy for hypotension; anesthetic or anesthetic adminiculum; remedy for sleep disorders represented by insomnia including increased sleep latency, intermittent wakefulness and decreased sleep efficiency; remedy for circadian rhythm disorder such as jet lag; drug for improving erectile function; airway dilation during dyspenea such as asthma or antitussive; or as drug for ameliorating motility of digestive tract during hypokinesis of digestive tract; their administration dosage or frequency differ depending on gender, age, body weight, degree of symptoms of individual patients and kind and extent of intended therapeutic effect. In general terms, for oral administration it is preferred to dispence 0.01–20 mg/kg per adult per day at a time or in a few times; and for parenteral administration, 0.002–10 mg/kg per day at a time or in a few times. Furthermore, it is also possible to administer them for prophylactic purpose, depending on symptoms of individual patients.

Best Modes for Carrying Out the Invention

Hereinafter the present invention is explained more specifically, referring to working Examples, it being understood that the invention is not limited to those working Examples. In the following, 1H-NMR was measured in all cases with $CDCl_3$ solution of each sample at 300 MHz, using tetramethylsilane as the reference substance.

PRODUCTION EXAMPLE 1

Productino of
1-(1,1,3,3-tetramethylbutyl)piperidin-4-one 1) 1-benzyl-1-methyl-4-oxopiperidinium iodide To 9.79 ml of 1-benzyl-4-piperidone, 16.5 ml of methyl iodide was added and stirred for 16 hours at room temperature. To the resulting yellow suspension, approx. 10 ml of ether was added and the formed yellow solid was recovered by filtration, which solid was washed with ether and dried to provide 13.42 g of the title compound as a yellow powder.

2) 1-(1,1,3,3-tetramethylbutyl)piperidin-4-one

To 1.20 ml of tert-octylamine, 10 ml of ethanol, 10 ml of an aqueous solution containing 580 mg of potassium carbonate and 3.31 g of 1-benzyl-1-methyl-4-oxopiperidinium iodide were successively added, followed by 2 hours' heating at 100° C. under stirring. The reaction liquid was cooled to room temperature, from which ethanol was distilled off under reduced pressure and the formed solution was diluted with water, followed by extraction with chloroform. The chloroform extract was dried over anhydrous magnesium sulfate, and the solvent was distilled off. The residue was separated and purified on silica gel column chromatography (hexane/ethyl acetate=5/1) to provide 500 mg of the title compound as a colorless oily substance.

PRODUCTION EXAMPLE 2

Production of 4-{[tert-butyl(diphenyl)silyl]oxy}-(2S* or 2R*)-2-[(3-fluorophenyl)amino]butanamide 1) (2S* or 2R*)-2-[(3-fluorophenyl)amino]-4-hydroxybutanamide A dimethylformamide solution (20 ml) of 1.93 ml of 3-fluoroaniline, 4.60 ml of α-bromo-γ-butyrolactone and 4.24 g of sodium carbonate was heated with stirring at 80° C. for 15 hours. The reaction liquid was cooled to room temperature, diluted with water and extracted with ether. The ether extract was dried over anhydrous magnesium sulfate, and thereafter the solvent was distilled off to provide 4.64 g of crude 3-[(3-fluorophenyl)amino]-dihydrofuran-2 (3H)-one as a pale yellow, oily substance.

This compound 4.64 g was dissolved in 15 ml of conc. aqueous ammonia and 60 ml of toluene, and the solution was stirred for 12 hours at room temperature. This reaction solution was concentrated under reduced pressure, to provide 4.74 g of crude 2-[(3-fluorophenyl)amino]-4-hydroxybutanamide as a pale yellow, oily substance. This crude product (3.68 g) was separated and purified on silica gel column chromatography (chloroform/methanol=50/4) to provide 2.32 g of a mixture of the title compounds as a yellow oily substance.

Said mixture (1.05 g) was separated and purified on high performance liquid chromatography [isopropanol/hexane/diisopropylamine=1/4/0.01; flow rate, 15 ml/min] using CIRALPAK-AD (DAISO). From the high polar fraction 554 mg of the title compound which is expediently referred to as 3S* configuration (optical purity: 87% ee) and from the low polar fraction 461 mg of the title compound which is expediently referred to as 3R* configuration (optical purity: 94% ee) were obtained, both as white solids, each of which was recrystallized from ethyl acetate-chloroform to provide 343 mg of 3S* configuration (optical purity: 99% ee) from 554 mg of the 3S* configuration (optical purity: 87% ee) and 366 mg of 3R* configuration (optical purity: 99% ee) from 461 mg of the 3R* configuration (optical purity: 94% ee), both as colorless needle-like crystals. Here the S* and R* symbols are provisionally assigned, because their stereostructures have not been specified, and ee is an abbreviation for enantiomeric excess.

2) 4-{[tert-butyl(diphenyl)silyl]oxy}-(2S* or 2R*)-2-[(3-fluorophenyl)-amino]butanamide A dimethylformamide solution (3 ml) of 300 mg of (2S*)-2-[(3-fluorophenyl)amino]-4-hydroxybutanamide, 0.44 ml of tert-butyl(diphenyl)silyl chloride and 241 mg of imidazole was stirred at room temperature for 3 days. Thus obtained reaction liquid was diluted with water and extracted with ether. The ether extract was successively washed with water, 10% aqueous citric acid solution and saturated brine, dried over anhydrous magnesium sulfate and the solvent was distilled off. The residue was separated and purified on silica gel chromatography (hexane/ethyl acetate=2/1) to provide 681 mg of the title compound (2S*) as a colorless oily substance.

Also using 300 mg of (2R*)-2-[(3-fluorophenyl)amino]-4-hydroxybutanamide, 642 mg of the title compound (2R*) was obtained through the same method, as a colorless oily substance.

EXAMPLE 1

Production of 4-(3-fluorophenyl)-(3S* or 3R*)-3-(2-hydroxyethyl)-8-(1,1,3,3-tetramethylbuty)-1,4,8-triazaspiro[4.5]decan-2-one

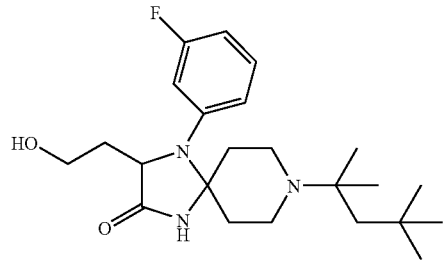

1) 3-((2S* or 2R*)-2-{[tert-butyl(diphenyl)silyl]oxy}ethyl)-4-(3-fluorophenyl)-8-(1,1,3,3-tetramethylbutyl)-1,4,8-triazaspiro[4.5]-decan-2-one Five (5) ml of 1,2-dichloroethane solution of 248 mg of 4-{[tert-butyl(diphenyl)silyl]oxy}-(2S*)-2-[(3-fluorophenyl)amino]butanamide, 106 mg of 1-(1,1,3,3-tetramethylbutyl)piperidin-4-one and 128 mg of camphorsulfonic acid was heated under reflux for 14 hours using Dean-Stark device to carry out a dehydration reaction. The reaction liquid was cooled to room temperature, diluted with chloroform and washed with 1N aqueous sodium hydroxide solution. The aqueous solution used for the washing was extracted with chloroform, the extract was combined with the earlier obtained chloroform extract, dried over anhydrous magnesium sulfate and the solvent was distilled off. The residue was separated and purified on silica gel column chromatography (hexane/ethyl acetate=3/1) to provide 176 mg of the title compound (2S*) as a colorless oily substance.

Using 248 mg of 4-{[tert-butyl(diphenyl)silyl]oxy}-(2R*)-2-[(3-fluorophenyl)amino]butanamide, 146 mg of the title compound (2R*) was obtained through the same method, as a colorless oily substance.

2) 4-(3-fluorophenyl)-(3S* or 3R*)-3-(2-hydroxyethyl)-8-(1,1,3,3-tetramethylbutyl)-1,4,8-triazaspiro[4.5]decan-2-one To a tetrahydrofuran solution (1 ml) of 162 mg of 3-((2S*)-2-{[tert-butyl(diphenyl)silyl]oxy}ethyl)-4-(3-fluorophenyl)-8-(1,1,3,3-tetramethylbutyl)-1,4,8-triazaspiro[4.5]-decan-2-one as obtained by (1), 1M tetrabutylammonium fluoride-tetrahydrofuran solution (1 ml) was added and heated under reflux for 30 minutes. The reaction solution was cooled to room temperature, and then concentrated under reduced pressure. The residue was dissolved in chloroform and washed with water. The washing was extracted with chloroform and the extract was combined with the earlier obtained chloroform extract, dried over anhydrous magnesium sulfate and the solvent was distilled off. The residue was separated and purified on silica gel column chromatography (ethyl acetate) to provide 31 mg of the title compound (2S*) as a colorless solid.

Using 136 mg of 3-((2R* -2-{[tert-butyl(diphenyl)silyl]-oxy}ethyl)-4-(3-fluorophenyl)-8-(1,1,3,3-tetramethylbutyl)-1,4,8-triazaspiro[4.5]-decan-2-one, 47 mg of the title compound (2R*) was obtained through the same method as a colorless solid.

(3R Configuration)
1H-NMR: 1.00 (9H, s), 1.09(6H, s), 1.04 (2H, s), 1.45 (1H, br), 1.78–1.97 (2H, m), 1.99–2.11 (2H, m), 2.12–2.26 (2H, m), 2.37–2.48 (1H, m), 3.02–3.20 (2H, m), 3.54–3.60 (1H, m), 3.77–3.83 (2H, m), 4.36 (1H, dd, j=2.9, 8.0 Hz), 6.68–6.81 (3H, m), 7.20–7.29 (1H, m), 7.61 (1H, brs)
EI-MS (+20 eV): 406.4

(3S Configuration)
1H-NMR: 1.00 (9H, s), 1.09 (6H, s), 1.04 (2H, s), 1.45 (1H, br), 1.78–1.97 (2H, m), 1.99–2.11 (2H, m), 2.12–2.26 (2H, m), 2.37–2.48 (1H, m), 3.02–3.20 (2H, m), 3.54–3.60 (1H, m), 3.77–3.83 (2H, m), 4.36 (1H, dd, j=2.9, 8.0 Hz), 6.68–6.81 (3H, m), 7.20–7.29 (1H, m), 7.61 (1H, brs)
EI-MS (+20 eV): 406.4

PRODUCTION EXAMPLE 3

Production of 2-[(3-fluorophenyl)amino]acetamide

An ethanol solution (50 ml) of 1.45 ml of 3-fluoroaniline and 1.37 g of 2-bromoacetamide was heated under reflux for 24 hours. The reaction liquid was cooled to room temperature and concentrated under reduced pressure. The residue was dissolved in chloroform and washed with 1N aqueous sodium hydroxide solution. The aqueous solution used for the washing was extracted with chloroform and combined with the earlier obtained chloroform extract, dried over anhydrous magnesium sulfate and the solvent was distilled off. The residue was separated and purified on silica gel column chromatography (chloroform/methanol=100/3) to provide 1.03 g of the title compound as a pale yellow solid.

EXAMPLE 2

Production of 4-(3-fluorophenyl)-8-(1,1,3,3-tetramethylbutyl)-1,4,8-triazaspiro[4.5]decan-2-one

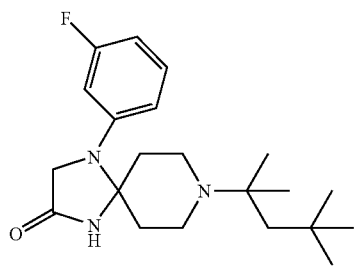

Example 1 was repeated except that 4-{[tert-butyl(diphenyl)silyl]oxy}-(2S*)-2-[(3-fluorophenyl)amino]butanamide which was used in Example 1 was replaced with 2-[(3-fluorophenyl)amino]acetamide as obtained in Production Example 3, to provide the title compound.
1H-NMR: 1.03 (9H, s), 1.12 (6H, s), 1.44 (2H, s), 1.53–1.64 (2H, m), 2.12–2.25 (2H, m), 2.69–2.82 (2H, m), 3.16–3.26 (2H, m), 3.92-(2H, s), 6.47–6.58 (3H, m) 7.15–7.24 (1H, m)
EI-MS(+20 eV): 362.2

PRODUCTION EXAMPLE 4

Production of 2-anilinoacetamide

Production Example 3 was repeated except that 3-fluoroaniline which was used in Production Example 3 was replaced with aniline, to provide the title compound.

EXAMPLE 3

Production of 4-phenyl-8-(1,1,3,3-tetramethylbutyl)-1,4,8-triazaspiro[4.5]decan-2-one

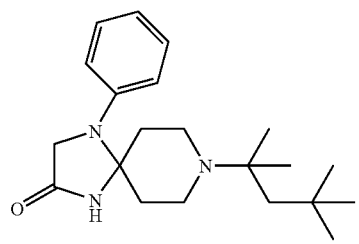

Example 1 was repeated except that 4-{[tert-butyl(diphenyl)-silyl]oxy}-(2S*)-2-[(3-fluorophenyl)amino]butanamide which was used in Example 1 was replaced with 2-anilinoacetamide as obtained in Production Example 4, to provide the title compound.
1H-NMR: 1.05 (9H, s), 1.12 (6H, s), 1.44 (2H, s), 1.53–1.63 (2H, m), 2.12–2.25 (2H, m), 2.65–2.78 (2H, dt), 3.12–3.22 (2H, m), 3.95 (2H, s), 6.81–6.89 (3H, m), 7.17–7.34 (3H, m)
EI-MS: 344.2[M+H]+

PRODUCTION EXAMPLE 5

Production of 1-(1-ethylpentyl)piperidin-4-one

A reaction was conducted by the same method as in Production Example 1–2) except that tert-octylamine which was used in Production Example 1–2) was replaced with 3-aminoheptane, to provide the title compound.

EXAMPLE 4

Production of 4-phenyl-8-(1-ethylpentyl)-1,4,8-triazaspiro[4.5]decan-2-one

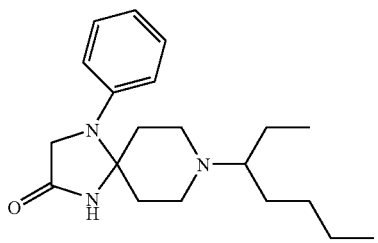

Example 1 was repeated except that 1-(1,1,3,3-tetramethylbutyl)piperidin-4-one which was used in Example 1 was replaced with 1-(1-ethylpentyl)piperidin-4-one as obtained in Production Example 5, and 4-{[tert-butyl(diphenyl)silyl]

oxy}-(2S*)-2-[(3-fluorophenyl)amino]butanam was replaced with 2-anilinoacetamide as obtained in Production Example 4, to provide the title compound.

1H-NMR: 0.94 (6H, t), 1.22–1.41 (6H, m), 1.41–1.55 (2H, m), 1.55–1.65 (2H, m), 2.27–2.37 (1H, m), 2.38–2.52 (2H, m), 2.63–2.77 (2H, m), 2.77–2.89 (2H, m), 3.97-(2H, s), 6.82–6.92 (3H, m), 7.25–7.33 (2H, m), 7.70 (1H, brs)

EI-MS: 330.2[M+H]$^+$

EXAMPLE 5

Production of 8-decahydranaphthalen-2-yl-4-phenyl-1,4,8-triazaspiro[4.5]decan-2-one

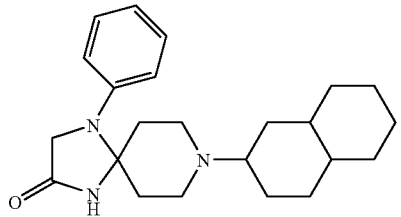

To a methanol solution (5 ml) of 4-phenyl-1,4,8-triazaspiro[4.5]decan-2-one (121 mg) as obtained in Production Example 4 and commercial 2-decalone (0.20 ml), sodium cyanoborohydride (52 mg) was added and stirred at room temperature for 5 hours. Then the reaction liquid was concentrated under reduced pressure, followed by addition of saturated aqueous sodium hydrogencarbonate solution and extraction with chloroform. The extract was washed with saturated brine, dried over anhydrous magnesium sulfate and the solvent was distilled off. The residue was separated and purified on silica gel column chromatography (chloroform/methanol=50/1) to provide 26 mg of the title compound as a pale yellow solid.

1H-NMR: 0.80–2.07 (18H, m), 2.33–2.47 (3H, m), 2.63–2.75 (2H, m), 2.96–3.05 (2H, m), 3.98 (2H, s), 6.84–6.93 (3H, m), 7.25–7.35 (2H, m), 8.00–8.10 (1H, m)

EI-MS: 368[M+H]

FORMULATION EXAMPLE 1

Using a V-type mixer, 20.0 g of the compound of Example 2, 417 g of lactose, 80 g of crystalline cellulose and 80 g of partial α-starch were mixed. Further 3.0 g of magnesium stearate was added and mixed, and the powdery mixture was tabletted following accepted practice to provide 3000 tablets of each 7.0 mm in diameter and 150 mg in weight.

| Ingredient contents per tablet (150 mg) | |
|---|---|
| Compound of Example 2 | 5.0 mg |
| Lactose | 104.25 mg |
| Crystalline cellulose | 20.0 mg |
| Partial α-starch | 20.0 mg |
| Magnesium stearate | 0.75 mg |

FORMULATION EXAMPLE 2

In 172.5 g of purified water, 10.8 g of Hydroxypropyl cellulose 2910 and 2.1 g of Polyethylene glycol 6000 were dissolved and in which 2.1 g of titanium dioxide was dispersed to provide a coating liquid. The coating liquid was spray-coated onto 2500 tablets of Formulation Example 1 which were separately prepared, with HICOATER MINI, to provide film-coated tablets weighing 155 mg per tablet.

| Ingredient contents per tablet | |
|---|---|
| Tablet of Formulation Example 1 | 150 mg |
| Hydroxypropyl cellulose 2910 | 3.6 mg |
| Polyethylene glycol 6000 | 0.7 mg |
| Titanium dioxide | 0.7 mg |

INDUSTRIAL APPLICABILITY

Compounds of the present invention possess high affinity to nociceptin receptor and hence act as agonist for nociceptin receptor and are useful as analgesic, reliever from tolerance to narcotic analgesic represented by morphine; reliever from dependence on narcotic analgesic represented by morphine; analgesic enhancer; antiobestic; drug for ameliorating brain function; remedy for schizophrenia; drug for treating regressive neurodegenerative diseases represented by Parkinsonism and chorea; antianxiety agent or antidepressant; remedy for diabetes insipidus; remedy for polyuria; remedy for hypotension; anesthetic or anesthetic adminiculum; remedy for sleep disorders represented by insomnia including increased sleep latency, intermittent wakefulness and decreased sleep efficiency; remedy for circadian rhythm disorder such as jet lag; drug for improving erectile function; airway dilation during dyspenea such as asthma or antitussive; or as drug for ameliorating motility of digestive tract during hypokinesis of digestive tract.

What is claimed is:

1. A 4-Oxoimidazolidine-2-spiropiperidine compound represented by formula [I]

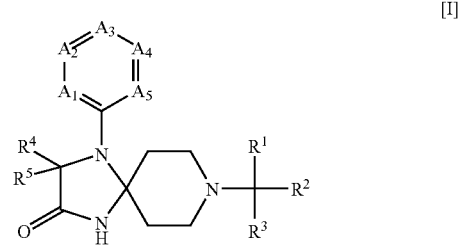

wherein $A_1$, $A_2$, $A_3$, $A_4$ and $A_5$ each independently stand for optionally halogen-substituted methine;

$R^1$ and $R^2$ each independently stand for lower alkyl;

$R^3$ stands for hydrogen or lower alkyl; and $R^4$ and $R^5$ each independently stand for hydrogen or optionally hydroxyl- or amino-substituted lower alkyl; or a salt thereof.

2. The compound or salt thereof as described in claim 1, wherein $A_1$, $A_2$, $A_3$, $A_4$ and $A_5$ are unsubstituted methine groups.

3. The compound or salt thereof as described in claim 1, wherein $R^1$ is methyl, and $R^2$ is n-butyl or 2,2-dimethylpropyl.

4. The compound or salt thereof as described in claim 1, wherein $R^1$ is ethyl and $R^2$ is n-butyl or 2,2-dimethylpropyl.

5. The compound or salt thereof as described in claim 3 or 4, wherein $R^3$ is hydrogen or methyl.

6. The compound or salt thereof as described in claim 1, wherein both $R^4$ and $R^5$ are hydrogen.

7. The compound or salt thereof as described in claim 1, wherein either one of $R^4$ and $R^5$ is hydrogen and the other is hydroxyl-substituted lower alkyl.

8. The compound or salt thereof as described in claim 7, wherein the lower alkyl of $R^4$ or $R^5$ is methyl or ethyl.

9. The compound or salt thereof as described in claim 1, wherein the 4-oxoimidazolidine-2-spiropiperidine compound is 4-(3-fluorophenyl)-3-(2-hydroxyethyl)-8-(1,1,3,3-tetramethylbutyl)-1,4,8-triazaspiro[4.5]decan-2-one, 4-(3-fluorophenyl)-8-(1,1,3,3-tetramethylbutyl)-1,4,8-triazaspiro[4.5]decan-2-one, 4-phenyl-8-(1,1,3,3-tetramethylbutyl)-1,4,8-triazaspiro[4.5]decan-2-one, or 4-phenyl-8-(1-ethylpentyl)-1,4,8-triazaspiro[4.5]decan-2-one.

10. A composition comprising the compound or salt thereof as described in claim 1,
and a pharmaceutically acceptable carrier.

* * * * *